(12) United States Patent
Francis

(10) Patent No.: US 11,266,538 B2
(45) Date of Patent: Mar. 8, 2022

(54) ADHESIVE WOUND DRESSING

(71) Applicant: Michael David Francis, Naples, FL (US)

(72) Inventor: Michael David Francis, Naples, FL (US)

(*) Notice: Subject to any disclaimer, the term of this patent is extended or adjusted under 35 U.S.C. 154(b) by 243 days.

(21) Appl. No.: 16/594,016

(22) Filed: Oct. 5, 2019

(65) Prior Publication Data

US 2020/0107966 A1 Apr. 9, 2020

Related U.S. Application Data

(60) Provisional application No. 62/742,419, filed on Oct. 7, 2018.

(51) Int. Cl.
| | | |
|---|---|---|
| *A61F 13/00* | (2006.01) | |
| *A61F 13/02* | (2006.01) | |
| *A61F 13/10* | (2006.01) | |
| *A61F 13/06* | (2006.01) | |

(52) U.S. Cl.
CPC ........ *A61F 13/025* (2013.01); *A61F 13/0266* (2013.01); *A61F 13/068* (2013.01); *A61F 13/105* (2013.01); *A61F 2013/00578* (2013.01); *A61F 2013/00604* (2013.01); *A61F 2013/00655* (2013.01)

(58) Field of Classification Search
CPC .. A61F 13/025; A61F 13/0266; A61F 13/068; A61F 13/105; A61F 2013/00578; A61F 2013/00604; A61F 2013/00655
See application file for complete search history.

(56) References Cited

U.S. PATENT DOCUMENTS

| | | | | |
|---|---|---|---|---|
| 2,389,831 A | * | 11/1945 | Welsh | A61F 13/105 2/21 |
| 3,132,648 A | * | 5/1964 | Scholl | A61F 13/105 128/894 |
| 3,263,681 A | * | 8/1966 | Nechtow | A61B 42/00 2/21 |
| 3,348,541 A | * | 10/1967 | Loebeck | A61F 13/105 602/58 |
| 7,779,483 B2 | * | 8/2010 | Berry | A41D 13/087 2/21 |
| 10,172,748 B1 | * | 1/2019 | Wanderman | A61F 13/068 |

* cited by examiner

*Primary Examiner* — Steven O Douglas
(74) *Attorney, Agent, or Firm* — Ariel S. Bentolila; Bay Area IP Group, LLC

(57) ABSTRACT

An adhesive wound dressing is disclosed herein. The adhesive wound dressing comprises a first layer that is an outer layer. A second layer is a resilient layer and affixed to an inner surface of the first layer. A third layer is an inner gauze dressing and affixed to an inner surface of the second layer, wherein the first layer, the second layer, and the third layer define a generally tubular configuration having an open end and a closed end. An adhesive layer may be applied adjacent to the open end for configured securing the adhesive wound dressing to a wounded body part subsequent to the wounded body part being inserted within the open end.

20 Claims, 13 Drawing Sheets

ADHESIVE WOUND DRESSING

CROSS-REFERENCE TO RELATED APPLICATIONS

The present Utility patent application claims priority benefit of the U.S. provisional application for patent Ser. No. 62/742,419 entitled "A HIGHLY CONFORMABLE ADHESIVE WOUND DRESSING FOR DISTAL EXTREMITIES", filed on 7 Oct. 2018 under 35 U.S.C. 119(e). The contents of this related provisional application are incorporated herein by reference for all purposes to the extent that such subject matter is not inconsistent herewith or limiting hereof.

RELATED CO-PENDING U.S. PATENT APPLICATIONS

N/A

INCORPORATION BY REFERENCE OF SEQUENCE LISTING PROVIDED AS A TEXT FILE

Not applicable.

FEDERALLY SPONSORED RESEARCH OR DEVELOPMENT

Not applicable.

REFERENCE TO SEQUENCE LISTING, A TABLE, OR A COMPUTER LISTING APPENDIX

Not applicable.

COPYRIGHT NOTICE

A portion of the disclosure of this patent document contains material that is subject to copyright protection by the author thereof. The copyright owner has no objection to the facsimile reproduction by anyone of the patent document or patent disclosure for the purposes of referencing as patent prior art, as it appears in the Patent and Trademark Office, patent file or records, but otherwise reserves all copyright rights whatsoever.

BACKGROUND OF THE RELEVANT PRIOR ART

One or more embodiments of the invention generally relate to an adhesive wound dressing. More particularly, certain embodiments of the invention relates to an adhesive wound dressing that may be applied to distal extremities of a human body.

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon. Conventionally, many different materials of diverse origins have been used to treat wounds by absorbing wound fluids and tissue from a wound site with different kinds of absorbent material. In recent times, the use of wound care products containing patches made of polymeric materials has become increasingly accepted practice in controlling different parameters associated with a wound site, e.g., water vapor, oxygen permeability, bacterial impermeability, and absorption of the wound fluids and tissues.

The following is an example of a specific aspect in the prior art that, while expected to be helpful to further educate the reader as to additional aspects of the prior art, is not to be construed as limiting the present invention, or any embodiments thereof, to anything stated or implied therein or inferred thereupon. By way of educational background, another aspect of the prior art generally useful to be aware of is that moisture-retentive wound dressings have become an increasingly accepted form of dressing in treating wounds, in particular pressure sores and ulcers. Different types of wound dressing structures have been developed in the art and generally include means for receiving, absorbing, and retaining the wound fluids and tissues. These means typically include polymeric foams, polymeric films, particulate and fibrous polymers, hydrogels, and hydrocolloids. These types of dressings are typically designed for covering wounds that occur on flat or substantially flat surfaces of the human body.

In view of the foregoing, it is clear that these traditional techniques are not perfect and leave room for more optimal approaches.

BRIEF DESCRIPTION OF THE DRAWINGS

The present invention is illustrated by way of example, and not by way of limitation, in the figures of the accompanying drawings and in which like reference numerals refer to similar elements and in which.

Figure 1:
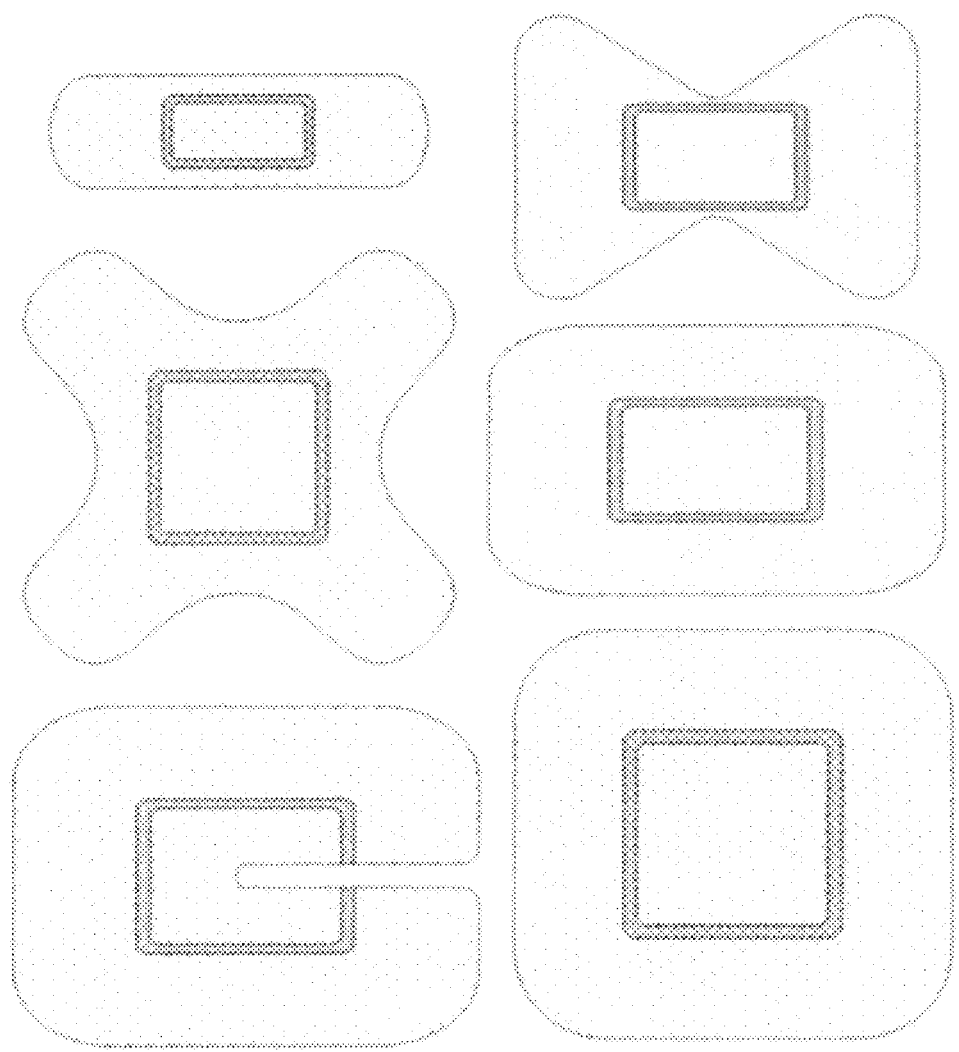
FIG. 1 illustrates schematic views of conventional adhesive wound dressings.
Figure 2A:
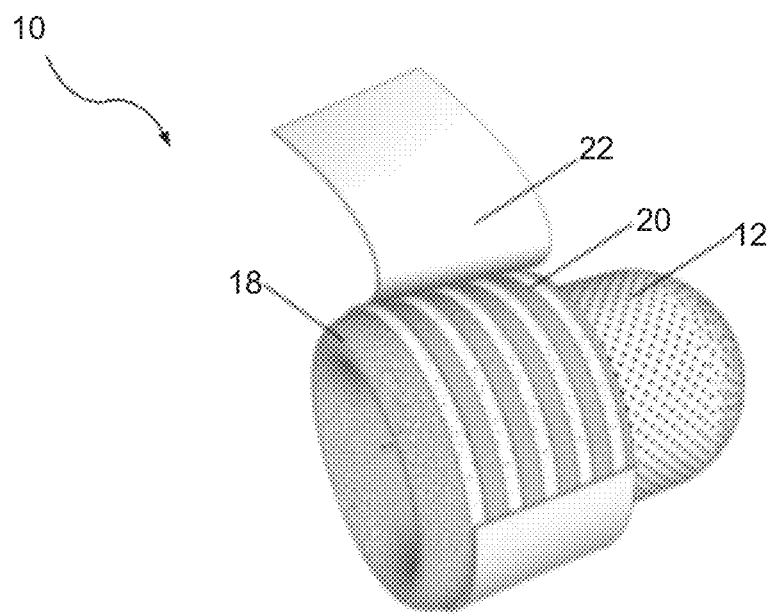
FIG. 2A through FIG. 3B illustrate different views of an adhesive wound dressing, in accordance with an embodiment of the present invention.
Figure 2B:
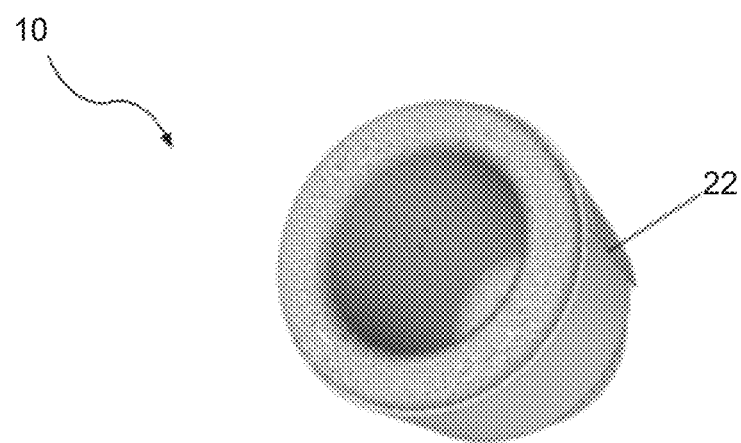
Figure 3A:
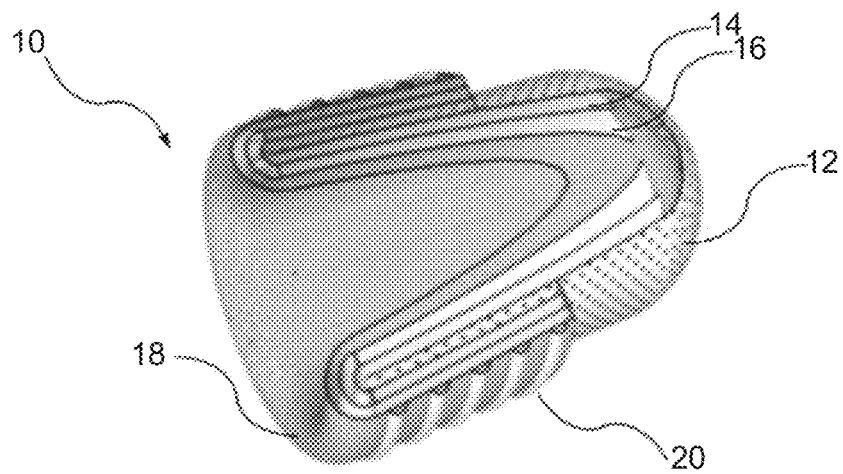
Figure 3B:
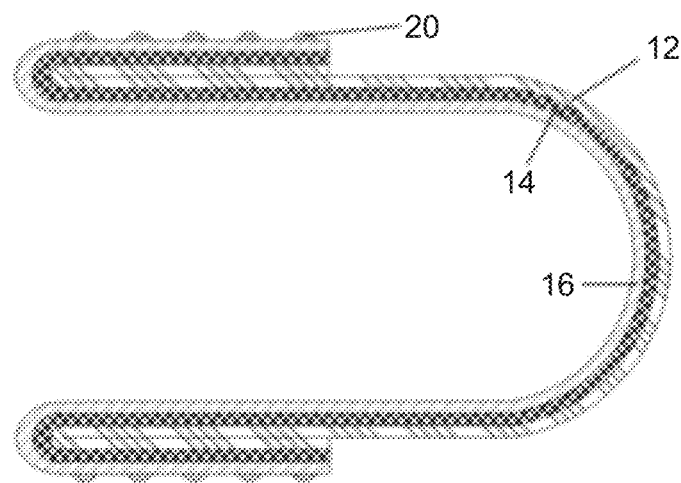

Unless otherwise indicated illustrations in the figures are not necessarily drawn to scale.

DETAILED DESCRIPTION OF SOME EMBODIMENTS

Embodiments of the invention are discussed below with reference to the Figures. However, those skilled in the art will readily appreciate that the detailed description given herein with respect to these figures is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

All words of approximation as used in the present disclosure and claims should be construed to mean "approximate," rather than "perfect," and may accordingly be employed as a meaningful modifier to any other word, specified parameter, quantity, quality, or concept. Words of approximation, include, yet are not limited to terms such as "substantial", "nearly", "almost", "about", "generally", "largely", "essentially", "closely approximate", etc.

As will be established in some detail below, it is well settled law, as early as 1939, that words of approximation are not indefinite in the claims even when such limits are not defined or specified in the specification.

For example, see Ex parte Mallory, 52 USPQ 297, 297 (Pat. Off. Bd. App. 1941) where the court said "The examiner has held that most of the claims are inaccurate because apparently the laminar film will not be entirely eliminated. The claims specify that the film is "substantially" eliminated and for the intended purpose, it is believed that the slight portion of the film which may remain is negligible. We are of the view, therefore, that the claims may be regarded as sufficiently accurate."

Note that claims need only "reasonably apprise those skilled in the art" as to their scope to satisfy the definiteness requirement. See Energy Absorption Sys., Inc. v. Roadway Safety Servs., Inc., Civ. App. 96-1264, slip op. at 10 (Fed. Cir. Jul. 3, 1997) (unpublished) Hybridtech v. Monoclonal Antibodies, Inc., 802 F.2d 1367, 1385, 231 USPQ 81, 94 (Fed. Cir. 1986), cert. denied, 480 U.S. 947 (1987). In addition, the use of modifiers in the claim, like "generally" and "substantial," does not by itself render the claims indefinite. See Seattle Box Co. v. Industrial Crating & Packing, Inc., 731 F.2d 818, 828-29, 221 USPQ 568, 575-76 (Fed. Cir. 1984).

Moreover, the ordinary and customary meaning of terms like "substantially" includes "reasonably close to: nearly, almost, about", connoting a term of approximation. See In re Frye, Appeal No. 2009-006013, 94 USPQ2d 1072, 1077, 2010 WL 889747 (B.P.A.I. 2010) Depending on its usage, the word "substantially" can denote either language of approximation or language of magnitude. Deering Precision Instruments, L.L.C. v. Vector Distribution Sys., Inc., 347 F.3d 1314, 1323 (Fed. Cir. 2003) (recognizing the "dual ordinary meaning of th[e] term ["substantially"] as connoting a term of approximation or a term of magnitude"). Here, when referring to the "substantially halfway" limitation, the Specification uses the word "approximately" as a substitute for the word "substantially" (Fact 4). (Fact 4). The ordinary meaning of "substantially halfway" is thus reasonably close to or nearly at the midpoint between the forwardmost point of the upper or outsole and the rearwardmost point of the upper or outsole.

Similarly, the term 'substantially' is well recognize in case law to have the dual ordinary meaning of connoting a term of approximation or a term of magnitude. See Dana Corp. v. American Axle & Manufacturing, Inc., Civ. App. 04-1116, 2004 U.S. App. LEXIS 18265, *13-14 (Fed. Cir. Aug. 27, 2004) (unpublished). The term "substantially" is commonly used by claim drafters to indicate approximation. See Cordis Corp. v. Medtronic AVE Inc., 339 F.3d 1352, 1360 (Fed. Cir. 2003) ("The patents do not set out any numerical standard by which to determine whether the thickness of the wall surface is 'substantially uniform.' The term 'substantially,' as used in this context, denotes approximation. Thus, the walls must be of largely or approximately uniform thickness."); see also Deering Precision Instruments, LLC v. Vector Distribution Sys., Inc., 347 F.3d 1314, 1322 (Fed. Cir. 2003); Epcon Gas Sys., Inc. v. Bauer Compressors, Inc., 279 F.3d 1022, 1031 (Fed. Cir. 2002). We find that the term "substantially" was used in just such a manner in the claims of the patents-in-suit: "substantially uniform wall thickness" denotes a wall thickness with approximate uniformity.

It should also be noted that such words of approximation as contemplated in the foregoing clearly limits the scope of claims such as saying 'generally parallel' such that the adverb 'generally' does not broaden the meaning of parallel. Accordingly, it is well settled that such words of approximation as contemplated in the foregoing (e.g., like the phrase 'generally parallel') envisions some amount of deviation from perfection (e.g., not exactly parallel), and that such words of approximation as contemplated in the foregoing are descriptive terms commonly used in patent claims to avoid a strict numerical boundary to the specified parameter. To the extent that the plain language of the claims relying on such words of approximation as contemplated in the foregoing are clear and uncontradicted by anything in the written description herein or the figures thereof, it is improper to rely upon the present written description, the figures, or the prosecution history to add limitations to any of the claim of the present invention with respect to such words of approximation as contemplated in the foregoing. That is, under such circumstances, relying on the written description and prosecution history to reject the ordinary and customary meanings of the words themselves is impermissible. See, for example, Liquid Dynamics Corp. v. Vaughan Co., 355 F.3d 1361, 69 USPQ2d 1595, 1600-01 (Fed. Cir. 2004). The plain language of phrase 2 requires a "substantial helical flow." The term "substantial" is a meaningful modifier implying "approximate," rather than "perfect." In Cordis Corp. v. Medtronic AVE, Inc., 339 F.3d 1352, 1361 (Fed. Cir. 2003), the district court imposed a precise numeric constraint on the term "substantially uniform thickness." We noted that the proper interpretation of this term was "of largely or approximately uniform thickness" unless something in the prosecution history imposed the "clear and unmistakable disclaimer" needed for narrowing beyond this simple-language interpretation. Id. In Anchor Wall Systems v. Rockwood Retaining Walls, Inc., 340 F.3d 1298, 1311 (Fed. Cir. 2003)" Id. at 1311. Similarly, the plain language of claim 1 requires neither a perfectly helical flow nor a flow that returns precisely to the center after one rotation (a limitation that arises only as a logical consequence of requiring a perfectly helical flow).

The reader should appreciate that case law generally recognizes a dual ordinary meaning of such words of approximation, as contemplated in the foregoing, as connoting a term of approximation or a term of magnitude; e.g., see Deering Precision Instruments, L.L.C. v. Vector Distrib. Sys., Inc., 347 F.3d 1314, 68 USPQ2d 1716, 1721 (Fed. Cir. 2003), cert. denied, 124 S. Ct. 1426 (2004) where the court was asked to construe the meaning of the term "substantially" in a patent claim. Also see Epcon, 279 F.3d at 1031 ("The phrase 'substantially constant' denotes language of approximation, while the phrase 'substantially below' signifies language of magnitude, i.e., not insubstantial."). Also, see, e.g., Epcon Gas Sys., Inc. v. Bauer Compressors, Inc., 279 F.3d 1022 (Fed. Cir. 2002) (construing the terms "substantially constant" and "substantially below"); Zodiac Pool Care, Inc. v. Hoffinger Indus., Inc., 206 F.3d 1408 (Fed. Cir. 2000) (construing the term "substantially inward"); York Prods., Inc. v. Cent. Tractor Farm & Family Ctr., 99 F.3d 1568 (Fed. Cir. 1996) (construing the term "substantially the entire height thereof"); Tex. Instruments Inc. v. Cypress Semiconductor Corp., 90 F.3d 1558 (Fed. Cir. 1996) (construing the term "substantially in the common plane"). In conducting their analysis, the court instructed to begin with the ordinary meaning of the claim terms to one of ordinary skill in the art. Prima Tek, 318 F.3d at 1148. Reference to dictionaries and our cases indicates that the term "substantially" has numerous ordinary meanings. As the district court stated, "substantially" can mean "significantly" or "considerably." The term "substantially" can also mean "largely" or "essentially." Webster's New 20th Century Dictionary 1817 (1983).

Words of approximation, as contemplated in the foregoing, may also be used in phrases establishing approximate ranges or limits, where the end points are inclusive and approximate, not perfect; e.g., see AK Steel Corp. v. Sollac, 344 F.3d 1234, 68 USPQ2d 1280, 1285 (Fed. Cir. 2003) where it where the court said "[W]e conclude that the ordinary meaning of the phrase "up to about 10%" includes the "about 10%" endpoint. As pointed out by AK Steel, when an object of the preposition "up to" is nonnumeric, the most natural meaning is to exclude the object (e.g., painting the wall up to the door). On the other hand, as pointed out by Sollac, when the object is a numerical limit, the normal meaning is to include that upper numerical limit (e.g., counting up to ten, seating capacity for up to seven passengers). Because we have here a numerical limit—"about 10%"—the ordinary meaning is that that endpoint is included.

In the present specification and claims, a goal of employment of such words of approximation, as contemplated in the foregoing, is to avoid a strict numerical boundary to the modified specified parameter, as sanctioned by Pall Corp. v. Micron Separations, Inc., 66 F.3d 1211, 1217, 36 USPQ2d 1225, 1229 (Fed. Cir. 1995) where it states "It is well established that when the term "substantially" serves reasonably to describe the subject matter so that its scope would be understood by persons in the field of the invention, and to distinguish the claimed subject matter from the prior art, it is not indefinite." Likewise see Verve LLC v. Crane Cams Inc., 311 F.3d 1116, 65 USPQ2d 1051, 1054 (Fed. Cir. 2002). Expressions such as "substantially" are used in patent documents when warranted by the nature of the invention, in order to accommodate the minor variations that may be appropriate to secure the invention. Such usage may well satisfy the charge to "particularly point out and distinctly claim" the invention, 35 U.S.C. § 112, and indeed may be necessary in order to provide the inventor with the benefit of his invention. In Andrew Corp. v. Gabriel Elecs. Inc., 847 F.2d 819, 821-22, 6 USPQ2d 2010, 2013 (Fed. Cir. 1988) the court explained that usages such as "substantially equal" and "closely approximate" may serve to describe the invention with precision appropriate to the technology and without intruding on the prior art. The court again explained in Ecolab Inc. v. Envirochem, Inc., 264 F.3d 1358, 1367, 60 USPQ2d 1173, 1179 (Fed. Cir. 2001) that "like the term 'about,' the term 'substantially' is a descriptive term commonly used in patent claims to 'avoid a strict numerical boundary to the specified parameter, see Ecolab Inc. v. Envirochem Inc., 264 F.3d 1358, 60 USPQ2d 1173, 1179 (Fed. Cir. 2001) where the court found that the use of the term "substantially" to modify the term "uniform" does not render this phrase so unclear such that there is no means by which to ascertain the claim scope.

Similarly, other courts have noted that like the term "about," the term "substantially" is a descriptive term commonly used in patent claims to "avoid a strict numerical boundary to the specified parameter."; e.g., see Pall Corp. v. Micron Seps., 66 F.3d 1211, 1217, 36 USPQ2d 1225, 1229 (Fed. Cir. 1995); see, e.g., Andrew Corp. v. Gabriel Elecs. Inc., 847 F.2d 819, 821-22, 6 USPQ2d 2010, 2013 (Fed. Cir. 1988) (noting that terms such as "approach each other," "close to," "substantially equal," and "closely approximate" are ubiquitously used in patent claims and that such usages, when serving reasonably to describe the claimed subject matter to those of skill in the field of the invention, and to distinguish the claimed subject matter from the prior art, have been accepted in patent examination and upheld by the courts). In this case, "substantially" avoids the strict 100% nonuniformity boundary.

Indeed, the foregoing sanctioning of such words of approximation, as contemplated in the foregoing, has been established as early as 1939, see Ex parte Mallory, 52 USPQ 297, 297 (Pat. Off. Bd. App. 1941) where, for example, the court said "the claims specify that the film is "substantially" eliminated and for the intended purpose, it is believed that the slight portion of the film which may remain is negligible. We are of the view, therefore, that the claims may be regarded as sufficiently accurate." Similarly, In re Hutchison, 104 F.2d 829, 42 USPQ 90, 93 (C.C.P.A. 1939) the court said "It is realized that "substantial distance" is a relative and somewhat indefinite term, or phrase, but terms and phrases of this character are not uncommon in patents in cases where, according to the art involved, the meaning can be determined with reasonable clearness."

Hence, for at least the forgoing reason, Applicants submit that it is improper for any examiner to hold as indefinite any claims of the present patent that employ any words of approximation.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be understood also to refer to functional equivalents of such structures. The present invention will be described in detail below with reference to embodiments thereof as illustrated in the accompanying drawings.

References to a "device," an "apparatus," a "system," etc., in the preamble of a claim should be construed broadly to mean "any structure meeting the claim terms" exempt for any specific structure(s)/type(s) that has/(have) been explicitly disavowed or excluded or admitted/implied as prior art in the present specification or incapable of enabling an object/aspect/goal of the invention. Furthermore, where the present specification discloses an object, aspect, function, goal, result, or advantage of the invention that a specific prior art structure and/or method step is similarly capable of performing yet in a very different way, the present invention disclosure is intended to and shall also implicitly include and cover additional corresponding alternative embodiments that are otherwise identical to that explicitly disclosed except that they exclude such prior art structure(s)/step(s), and shall accordingly be deemed as providing sufficient disclosure to support a corresponding negative limitation in a claim claiming such alternative embodiment(s), which exclude such very different prior art structure(s)/step(s) way(s).

From reading the present disclosure, other variations and modifications will be apparent to persons skilled in the art. Such variations and modifications may involve equivalent and other features which are already known in the art, and which may be used instead of or in addition to features already described herein.

Although Claims have been formulated in this Application to particular combinations of features, it should be understood that the scope of the disclosure of the present invention also includes any novel feature or any novel combination of features disclosed herein either explicitly or implicitly or any generalization thereof, whether or not it relates to the same invention as presently claimed in any Claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable subcombination. The Applicants hereby give notice that new Claims may be formulated to such features and/or combinations of such features during the prosecution of the present Application or of any further Application derived therefrom.

References to "one embodiment," "an embodiment," "example embodiment," "various embodiments," "some embodiments," "embodiments of the invention," etc., may indicate that the embodiment(s) of the invention so described may include a particular feature, structure, or characteristic, but not every possible embodiment of the invention necessarily includes the particular feature, structure, or characteristic. Further, repeated use of the phrase "in one embodiment," or "in an exemplary embodiment," "an embodiment," do not necessarily refer to the same embodiment, although they may. Moreover, any use of phrases like "embodiments" in connection with "the invention" are never meant to characterize that all embodiments of the invention must include the particular feature, structure, or characteristic, and should instead be understood to mean "at least some embodiments of the invention" include the stated particular feature, structure, or characteristic.

References to "user", or any similar term, as used herein, may mean a human or non-human user thereof. Moreover, "user", or any similar term, as used herein, unless expressly stipulated otherwise, is contemplated to mean users at any stage of the usage process, to include, without limitation, direct user(s), intermediate user(s), indirect user(s), and end user(s). The meaning of "user", or any similar term, as used herein, should not be otherwise inferred or induced by any pattern(s) of description, embodiments, examples, or referenced prior-art that may (or may not) be provided in the present patent.

References to "end user", or any similar term, as used herein, is generally intended to mean late stage user(s) as opposed to early stage user(s). Hence, it is contemplated that there may be a multiplicity of different types of "end user" near the end stage of the usage process. Where applicable, especially with respect to distribution channels of embodiments of the invention comprising consumed retail products/services thereof (as opposed to sellers/vendors or Original Equipment Manufacturers), examples of an "end user" may include, without limitation, a "consumer", "buyer", "customer", "purchaser", "shopper", "enjoyer", "viewer", or individual person or non-human thing benefiting in any way, directly or indirectly, from use of. or interaction, with some aspect of the present invention.

In some situations, some embodiments of the present invention may provide beneficial usage to more than one stage or type of usage in the foregoing usage process. In such cases where multiple embodiments targeting various stages of the usage process are described, references to "end user", or any similar term, as used therein, are generally intended to not include the user that is the furthest removed, in the foregoing usage process, from the final user therein of an embodiment of the present invention.

Where applicable, especially with respect to retail distribution channels of embodiments of the invention, intermediate user(s) may include, without limitation, any individual person or non-human thing benefiting in any way, directly or indirectly, from use of, or interaction with, some aspect of the present invention with respect to selling, vending, Original Equipment Manufacturing, marketing, merchandising, distributing, service providing, and the like thereof.

References to "person", "individual", "human", "a party", "animal", "creature", or any similar term, as used herein, even if the context or particular embodiment implies living user, maker, or participant, it should be understood that such characterizations are sole by way of example, and not limitation, in that it is contemplated that any such usage, making, or participation by a living entity in connection with making, using, and/or participating, in any way, with embodiments of the present invention may be substituted by such similar performed by a suitably configured non-living entity, to include, without limitation, automated machines, robots, humanoids, computational systems, information processing systems, artificially intelligent systems, and the like. It is further contemplated that those skilled in the art will readily recognize the practical situations where such living makers, users, and/or participants with embodiments of the present invention may be in whole, or in part, replaced with such non-living makers, users, and/or participants with embodiments of the present invention. Likewise, when those skilled in the art identify such practical situations where such living makers, users, and/or participants with embodiments of the present invention may be in whole, or in part, replaced with such non-living makers, it will be readily apparent in light of the teachings of the present invention how to adapt the described embodiments to be suitable for such non-living makers, users, and/or participants with embodiments of the present invention. Thus, the invention is thus to also cover all such modifications, equivalents, and alternatives falling within the spirit and scope of such adaptations and modifications, at least in part, for such non-living entities.

Headings provided herein are for convenience and are not to be taken as limiting the disclosure in any way.

The enumerated listing of items does not imply that any or all of the items are mutually exclusive, unless expressly specified otherwise.

It is understood that the use of specific component, device and/or parameter names are for example only and not meant to imply any limitations on the invention. The invention may thus be implemented with different nomenclature/terminology utilized to describe the mechanisms/units/structures/components/devices/parameters herein, without limitation. Each term utilized herein is to be given its broadest interpretation given the context in which that term is utilized.

Terminology. The following paragraphs provide definitions and/or context for terms found in this disclosure (including the appended claims):

"Comprising" And "contain" and variations of them— Such terms are open-ended and mean "including but not limited to". When employed in the appended claims, this term does not foreclose additional structure or steps. Consider a claim that recites: "A memory controller comprising a system cache . . . ." Such a claim does not foreclose the memory controller from including additional components (e.g., a memory channel unit, a switch).

"Configured To." Various units, circuits, or other components may be described or claimed as "configured to" perform a task or tasks. In such contexts, "configured to" or "operable for" is used to connote structure by indicating that the mechanisms/units/circuits/components include structure (e.g., circuitry and/or mechanisms) that performs the task or tasks during operation. As such, the mechanisms/unit/circuit/component can be said to be configured to (or be operable) for perform(ing) the task even when the specified mechanisms/unit/circuit/component is not currently operational (e.g., is not on). The mechanisms/units/circuits/components used with the "configured to" or "operable for" language include hardware—for example, mechanisms, structures, electronics, circuits, memory storing program instructions executable to implement the operation, etc. Reciting that a mechanism/unit/circuit/component is "configured to" or "operable for" perform(ing) one or more tasks is expressly intended not to invoke 35 U.S.C. sctn.112, sixth paragraph, for that mechanism/unit/circuit/component. "Configured to" may also include adapting a manufacturing process to fabricate devices or components that are adapted to implement or perform one or more tasks.

"Based On." As used herein, this term is used to describe one or more factors that affect a determination. This term does not foreclose additional factors that may affect a determination. That is, a determination may be solely based on those factors or based, at least in part, on those factors. Consider the phrase "determine A based on B." While B may be a factor that affects the determination of A, such a phrase does not foreclose the determination of A from also being based on C. In other instances, A may be determined based solely on B.

The terms "a", "an" and "the" mean "one or more", unless expressly specified otherwise.

All terms of exemplary language (e.g., including, without limitation, "such as", "like", "for example", "for instance", "similar to", etc.) are not exclusive of any other, potentially, unrelated, types of examples; thus, implicitly mean "by way of example, and not limitation . . . ", unless expressly specified otherwise.

Unless otherwise indicated, all numbers expressing conditions, concentrations, dimensions, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phase "consisting essentially of" and "consisting of" limits the scope of a claim to the specified elements or method steps, plus those that do not materially affect the basis and novel characteristic(s) of the claimed subject matter (see Norian Corp. v Stryker Corp., 363 F.3d 1321, 1331-32, 70 USPQ2d 1508, Fed. Cir. 2004). Moreover, for any claim of the present invention which claims an embodiment "consisting essentially of" or "consisting of" a certain set of elements of any herein described embodiment it shall be understood as obvious by those skilled in the art that the present invention also covers all possible varying scope variants of any described embodiment(s) that are each exclusively (i.e., "consisting essentially of") functional subsets or functional combination thereof such that each of these plurality of exclusive varying scope variants each consists essentially of any functional subset(s) and/or functional combination(s) of any set of elements of any described embodiment(s) to the exclusion of any others not set forth therein. That is, it is contemplated that it will be obvious to those skilled how to create a multiplicity of alternate embodiments of the present invention that simply consisting essentially of a certain functional combination of elements of any described embodiment(s) to the exclusion of any others not set forth therein, and the invention thus covers all such exclusive embodiments as if they were each described herein.

With respect to the terms "comprising," "consisting of," and "consisting essentially of," where one of these three terms is used herein, the disclosed and claimed subject matter may include the use of either of the other two terms. Thus in some embodiments not otherwise explicitly recited, any instance of "comprising" may be replaced by "consisting of" or, alternatively, by "consisting essentially of", and thus, for the purposes of claim support and construction for "consisting of" format claims, such replacements operate to create yet other alternative embodiments "consisting essentially of" only the elements recited in the original "comprising" embodiment to the exclusion of all other elements.

Moreover, any claim limitation phrased in functional limitation terms covered by 35 USC § 112(6) (post AIA 112(f)) which has a preamble invoking the closed terms "consisting of," or "consisting essentially of," should be understood to mean that the corresponding structure(s) disclosed herein define the exact metes and bounds of what the so claimed invention embodiment(s) consists of, or consisting essentially of, to the exclusion of any other elements which do not materially affect the intended purpose of the so claimed embodiment(s).

Devices or system modules that are in at least general communication with each other need not be in continuous communication with each other, unless expressly specified otherwise. In addition, devices or system modules that are in at least general communication with each other may communicate directly or indirectly through one or more intermediaries. Moreover, it is understood that any system components described or named in any embodiment or claimed herein may be grouped or sub-grouped (and accordingly implicitly renamed) in any combination or sub-combination as those skilled in the art can imagine as suitable for the particular application, and still be within the scope and spirit of the claimed embodiments of the present invention. For an example of what this means, if the invention was a controller of a motor and a valve and the embodiments and claims articulated those components as being separately grouped and connected, applying the foregoing would mean that such an invention and claims would also implicitly cover the valve being grouped inside the motor and the controller being a remote controller with no direct physical connection to the motor or internalized valve, as such the claimed invention is contemplated to cover all ways of grouping and/or adding of intermediate components or systems that still substantially achieve the intended result of the invention.

A description of an embodiment with several components in communication with each other does not imply that all such components are required. On the contrary a variety of optional components are described to illustrate the wide variety of possible embodiments of the present invention.

As is well known to those skilled in the art many careful considerations and compromises typically must be made when designing for the optimal manufacture of a commercial implementation any system, and in particular, the embodiments of the present invention. A commercial implementation in accordance with the spirit and teachings of the present invention may configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

Adhesive wound dressings are known in the art. Some examples of the conventional adhesive wound dressings are illustrated in FIG. 1. The conventional adhesive wound dressing structures include the usage of polymeric foams, polymeric films, particulate and fibrous polymers, hydrogels, and hydrocolloids for absorbing wound fluids and tissues. A disadvantageous aspect of the conventional adhesive dressings is that the conventional adhesive wound dressings are typically designed for covering wounds that occur on substantially flat locations on the human body. These conventional adhesive wound dressings are not suitable for application on distal extremities of the human body such as the tip on the fingers and toes because these adhesive wound dressings, as these distal extremities typically have a curved profile.

At least one embodiment of the present invention is directed towards an adhesive wound dressing for treating wounds generally occurring on distal extremities of the human body, which typically have curved, irregular, cylindrical, compound, moving or uneven surfaces. An aspect of an adhesive wound dressing is that a certain pre-determined tension is advantageous for treating the wound in order to limit the fluid outflow from the wound as well as to absorb the fluid exiting the wound. At least one embodiment of the present invention is directed towards an adhesive wound dressing that may be configured to snugly fit onto the distal extremity of the human body, e.g., fingers or toes, while applying some tension onto the wound. At least one embodiment of the present invention is directed towards an adhesive wound dressing that may have an elastic and stretchable configuration.

The present invention is best understood by reference to the detailed figures and description set forth herein.

Reference is hereinafter directed to FIG. 2A through FIG. 4B. Different views of an adhesive wound dressing 10, in accordance with an embodiment of the present invention are illustrated in FIG. 2A through FIG. 4B. The adhesive wound dressing, in accordance with an embodiment of the present invention, comprises a first layer 12. In one embodiment, the first layer may include a water proof coating. In another embodiment, the first layer may also include and at least one gripping portion to provide the user with a grip similar to when the user is not wearing any kind of wound dressing. In accordance with one embodiment, the first layer may be an outer braided shell. The adhesive wound dressing further comprises a second layer 14. In accordance with one embodiment, the second layer may be an inner scrim shell. The adhesive wound dressing further comprises a third layer. In accordance with an embodiment, the third layer may be an inner gauze dressing 16. An advantageous aspect of the inner gauze dressing is that the inner gauze dressing is the portion of the adhesive wound dressing coming in contact with the wound for treating the wound while absorbing wound fluids and tissues.

In accordance with one embodiment, the adhesive wound dressing may have a cylindrical configuration which is closed at one end. More specifically, the adhesive wound dressing may be shaped into the cylindrical shape after all of the layers, i.e., the first layer, the second layer, and the third layer of the adhesive wound dressing are assembled together. In one exemplary embodiment, the first layer, the second layer, and the third layer may be assembled together via pressing operation, which may involve the first, second, and third layers to pass through a series of rollers. Subsequent to the pressing of the first, second, and third layers, punching operation may be performed thereon for obtaining the hollow cylindrical shape, within which a finger or a toe may be accommodated.

The adhesive wound dressing, in accordance with one embodiment, may be folded at the bottom to define a folded portion 18. The folding allows a portion of an inner surface of the adhesive wound dressing to be exposed inside out. In accordance with one embodiment of the present invention, an adhesive layer 20 may be provided at the folded portion. In accordance with an embodiment of the present invention, the adhesive may be pressure-sensitive, non-allergenic, and sterile. Examples of adhesive layer may include acrylic or rubber based adhesive formulations. An advantageous aspect of the adhesive layer being provided on the folded portion is that a user may insert a wounded part of the body, e.g., a wounded finger, within the adhesive wound dressing, and the folded portion may then be unfolded to allow the adhesive layer contact the skin of the user to secure the adhesive wound dressing onto the finger. In accordance with one embodiment, the adhesive layer may be provided on the folded portion in different configurations, including but not limited to, spaced apart adhesive rings, adhesive layer of a pre-determined thickness, intermittently placed adhesive blocks, and the like.

Figure 4A:
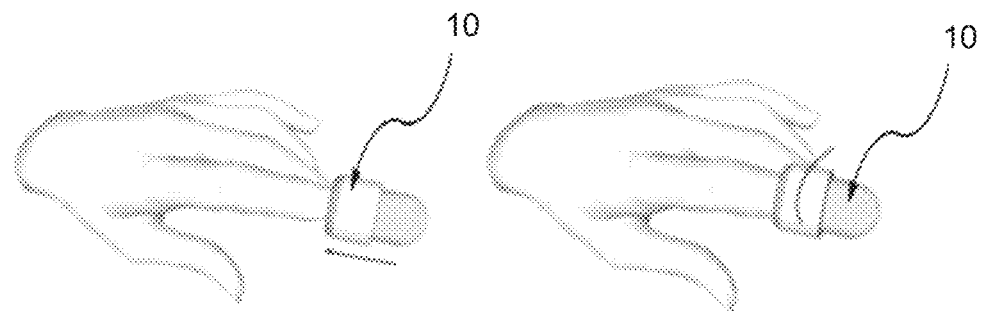
FIG. 4A and FIG. 4B illustrate perspective views depicting the adhesive wound dressing, in accordance with an embodiment of the present invention, being deployed on a user's finger.
Figure 4B:
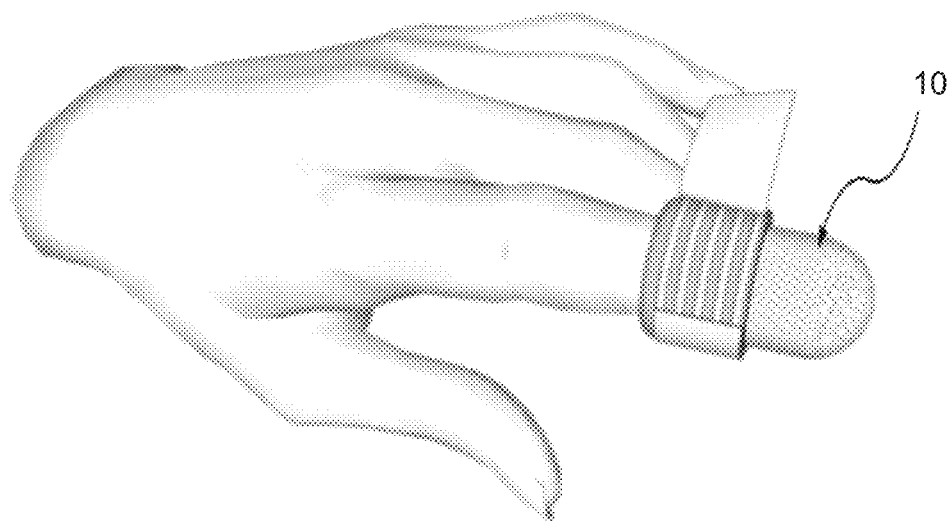
Figure 5A:
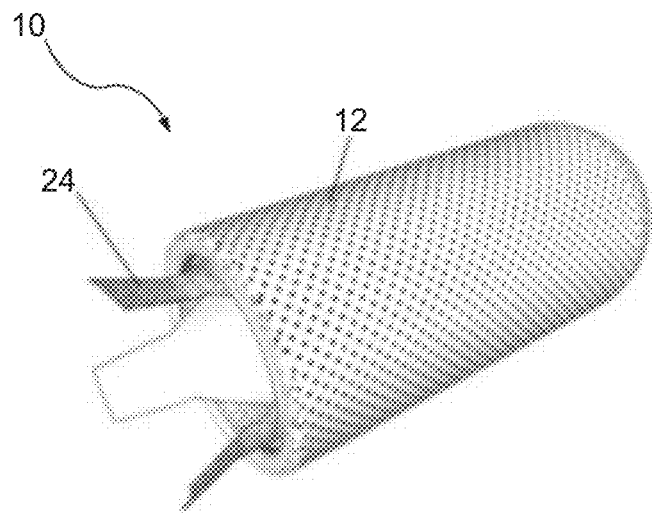
FIG. 5A through FIG. 6B illustrate different views of an adhesive wound dressing, in accordance with another embodiment of the present invention.
Figure 5B:
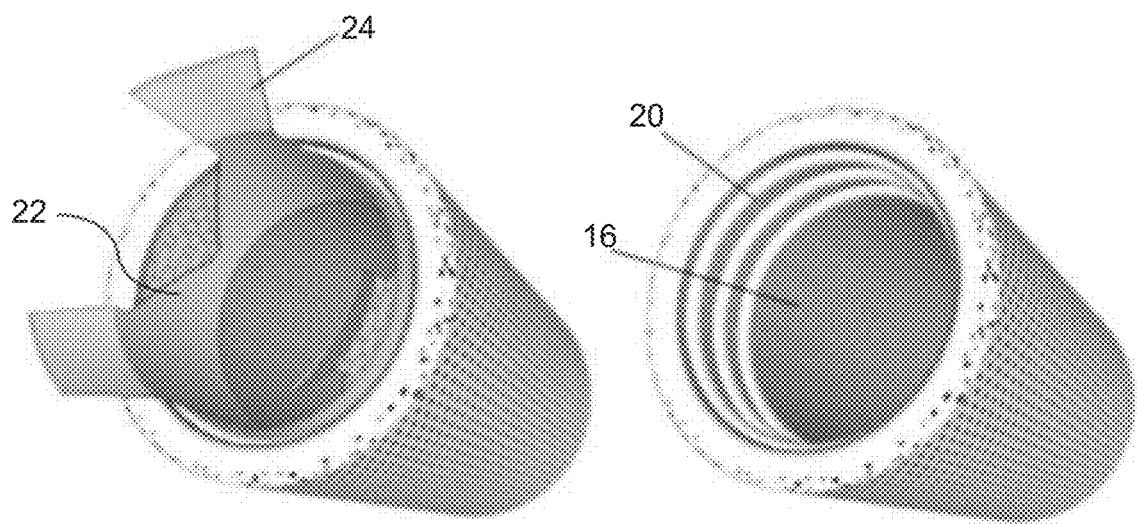
Figure 6A:
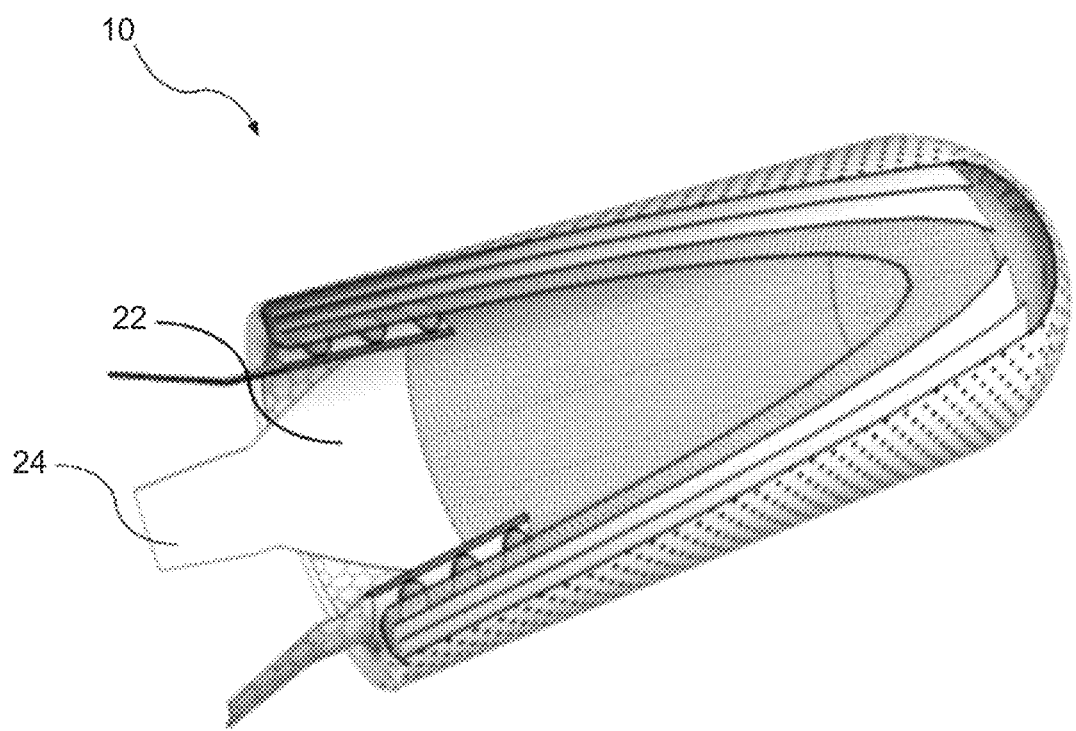
Figure 6B:
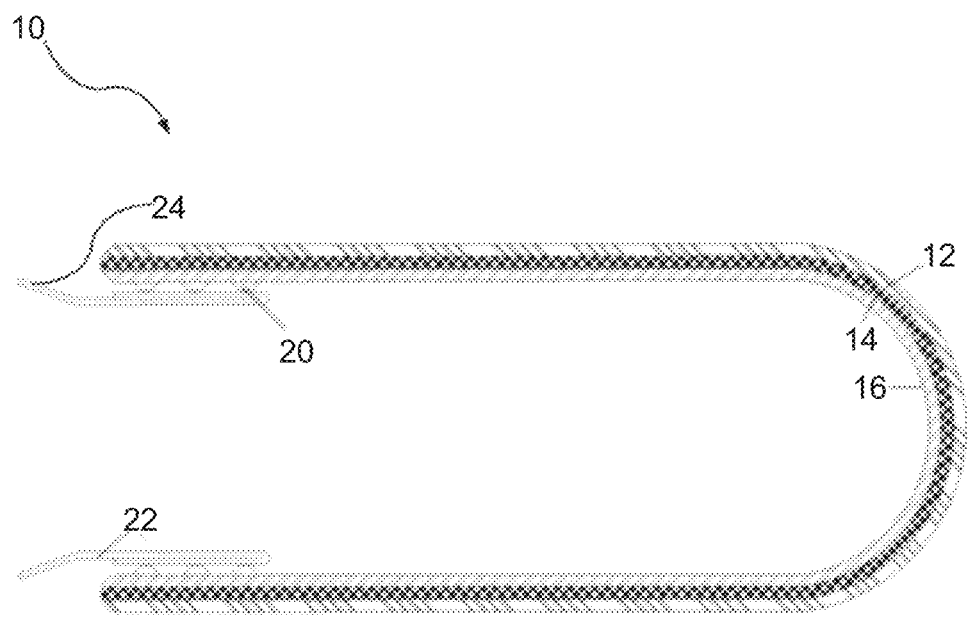
Figure 7A:
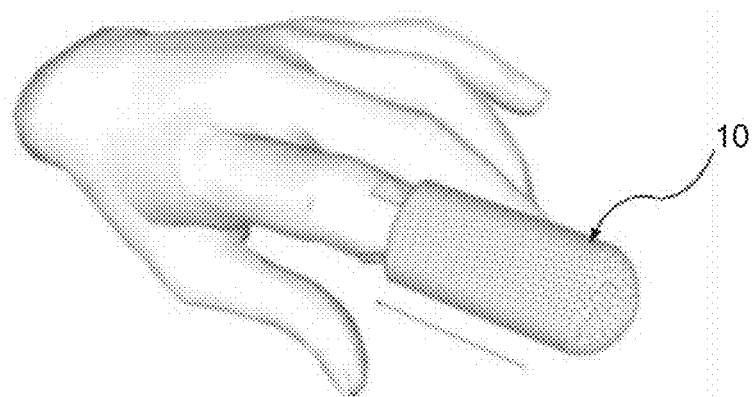
FIG. 7A and FIG. 8B illustrate perspective views depicting the adhesive wound dressing, in accordance with an embodiment of the present invention, being deployed on a user's finger.
Figure 7B:
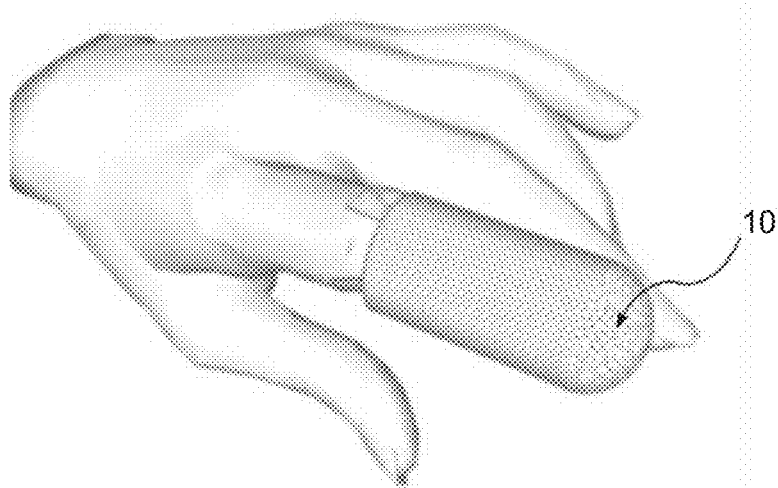
Figure 8A:
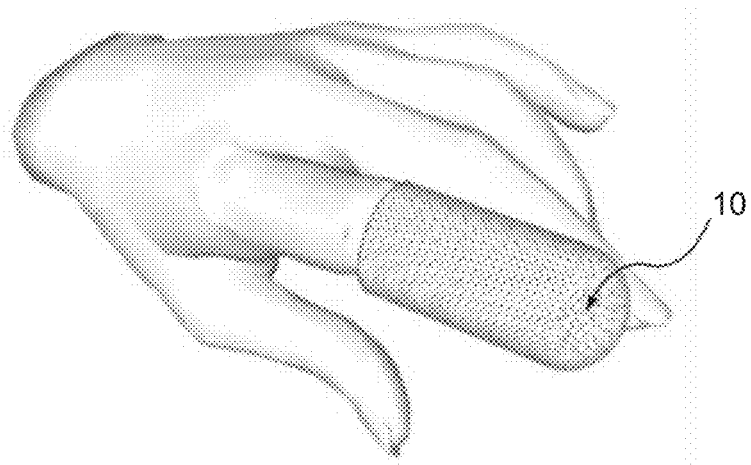
Figure 8B:
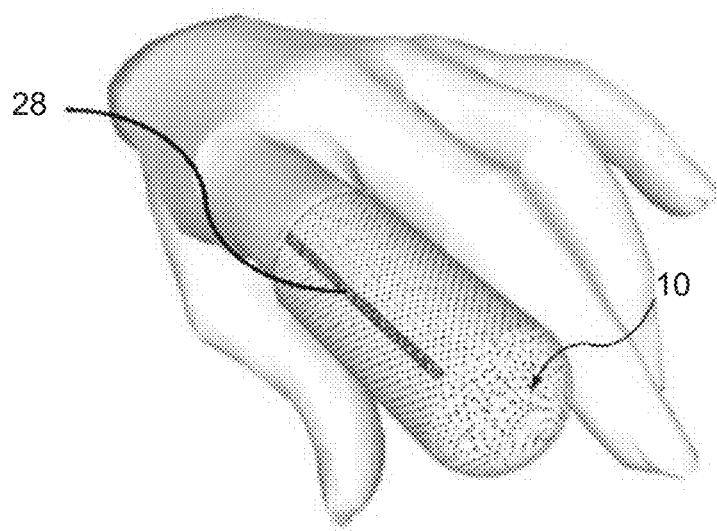

In one embodiment, the adhesive layer may be covered with a removable paper backing 22 which protects the adhesive layer prior to deployment. FIG. 4A and FIG. 4B depict the steps involved in deploying the adhesive wound dressing, in accordance with an embodiment of the present invention. As seen in FIG. 4A and FIG. 4B, a wounded finger may be inserted within the adhesive wound dressing. Once the user adjusts the position of the finger within the adhesive wound dressing, the removable paper backing may be removed to expose the adhesive layer. Once the adhesive layer is exposed, the folded portion may be unfolded to allow the adhesive to contact the skin to secure the wound dressing in place.

Another embodiment of an adhesive wound dressing is illustrated in FIG. 5A through FIG. 8B. As seen in FIG. 6A and FIG. 6B, the adhesive layer may be provided adjacent an open end of the adhesive wound dressing and on the inner surface of the adhesive wound dressing. The open end of the adhesive wound dressing is that end in which a wounded body part is to be inserted. As seen in FIG. 7A through FIG. 8B, the removable backing paper has tabs 24 that can be used to remove the removable backing paper subsequent to the wounded body part being inserted in the adhesive wound dressing. Once the removable backing paper is removed, the adhesive layer may contact the skin to secure the adhesive wound dressing in place.

Figure 9A:
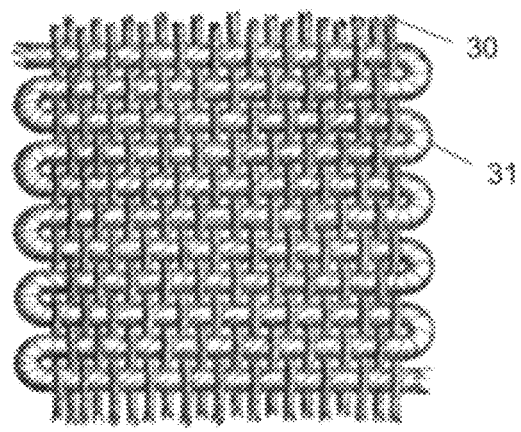
FIG. 9A illustrates a schematic view of a scrim material used in the conventional adhesive dressings.

A schematic view of a scrim material used in the conventional adhesive dressings is illustrated in FIG. 9A. As seen in FIG. 9A, the yarns for the scrim material has one or more wefts 31 arranged perpendicular to one or more warps 30. The yarn configuration illustrated in FIG. 9A is suitable for conventional adhesive wound dressings since the conventional adhesive wound dressings are typically designed to be applied on substantially flat areas on the human body. As such, it is not required for the yarn of the scrim material to have an elastic and stretchable configuration.

Figure 9B:
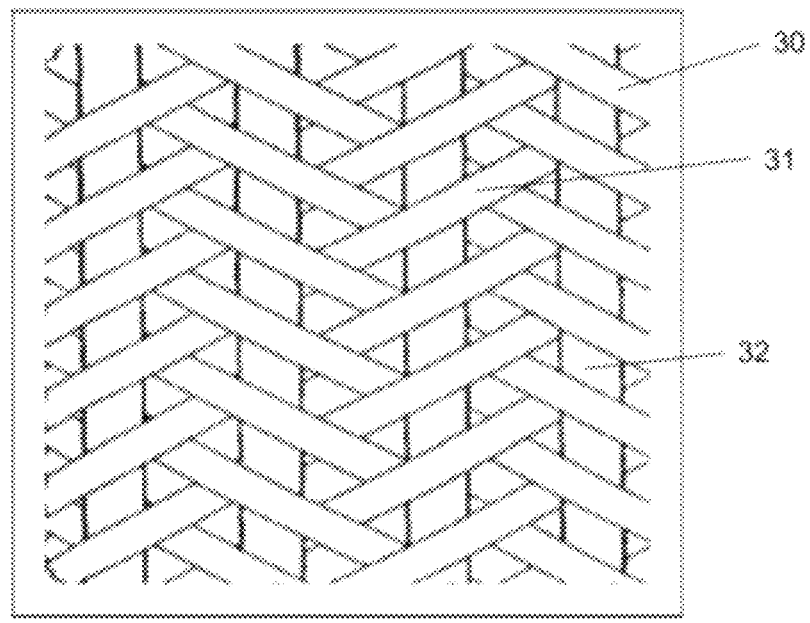
FIG. 9B illustrates a schematic view of a scrim material used in an adhesive wound dressing, in accordance with an embodiment of the present invention.

FIG. 9B illustrates a schematic view of a scrim material used in an adhesive wound dressing, in accordance with an embodiment of the present invention. As seen in FIG. 9B, the yarns for the scrim material may be arranged in a bias-weave or 'braided' fashion, i.e., diagonally to the longitudinal edge thereof. In accordance with one embodiment, the warp 30 and the weft 31 may be at an angle of 45° to the machine direction of the tube. An advantageous aspect of such a yarn is that it provides the adhesive wound dressing device with inherent stretch and elasticity to apply some amount of tension on the wound when deployed. In accordance with an embodiment of the present invention, at least one of the first and the second layers of the adhesive wound dressing may be made using the bias weaved yarn. An advantageous aspect of the adhesive wound dressing that includes the usage of the bias-weave yarn is that when stretched around a compound curve, irregular, moving or uneven surface, e.g., a finger or a toe, may do so with greater conformity and tension than relative to the conventional 'flat', 'planar', or 'laminar' wound dressings. Another advantageous aspect of the usage of the bias weave yarn is that the dressing may narrow in width by virtue of the bi-axial braiding, thereby imparting compressional transverse force. The compressional transverse force is applied along the length of the adhesive wound dressing on the wounded body part. Such a feature is advantageous in wearable wound devices that are required to maintain intimate contact with wound at the wounded body part, for example in applications for fingers, toes, and the like. In accordance with one embodiment, the second layer is a hollow bi-axially braided cloth scrim comprising interlocking fibers oriented to provide elasticity in at least two directions, wherein the tubular hollow bi-axially braided cloth scrim is laminated to the first layer. In accordance with another embodiment, the second layer includes tubular hollow bi-axially braided cloth scrims configured at discrete locations along the length of the adhesive wound dressing, thereby providing resilience and elasticity to the adhesive wound dressing to secure the adhesive wound dressing on the wounded body part of compound shapes.

Reference is hereinafter directed to FIG. 11. In accordance with one embodiment, the first layer or a pliable outer layer may be extruded on to the second layer or the scrim. In one embodiment, the pliable outer layer of the first layer may be on the order of 4-6 microns thick and may be made of a known flexible plastic support material. In accordance with one embodiment, the scrim or the second layer may be on the order of 2-8 microns thick. In accordance with one embodiment, the bias weave yarns or bi-axially braided yarns may be made from various types of natural and synthetic fibers. In accordance with one embodiment, for flexibility of the second layer or the scrim may have a low thread count to allow the same to be in taped roll form. In accordance with one embodiment, the adhesive layer may be on the order of 3-6 microns thick.

In accordance with another embodiment, the adhesive wound dressing may be assembled by individually producing and sequentially coating the different layers. For example, the first layer or the pliable outer layer and the second layer or the braided scrim may be individually supplied to an extruder to provide a tubular structure of these two components. Adhesive layer may then be coated radially thereon by known coating techniques. Removable paper backing may be applied on the adhesive layer by known web application techniques.

Figure 10:
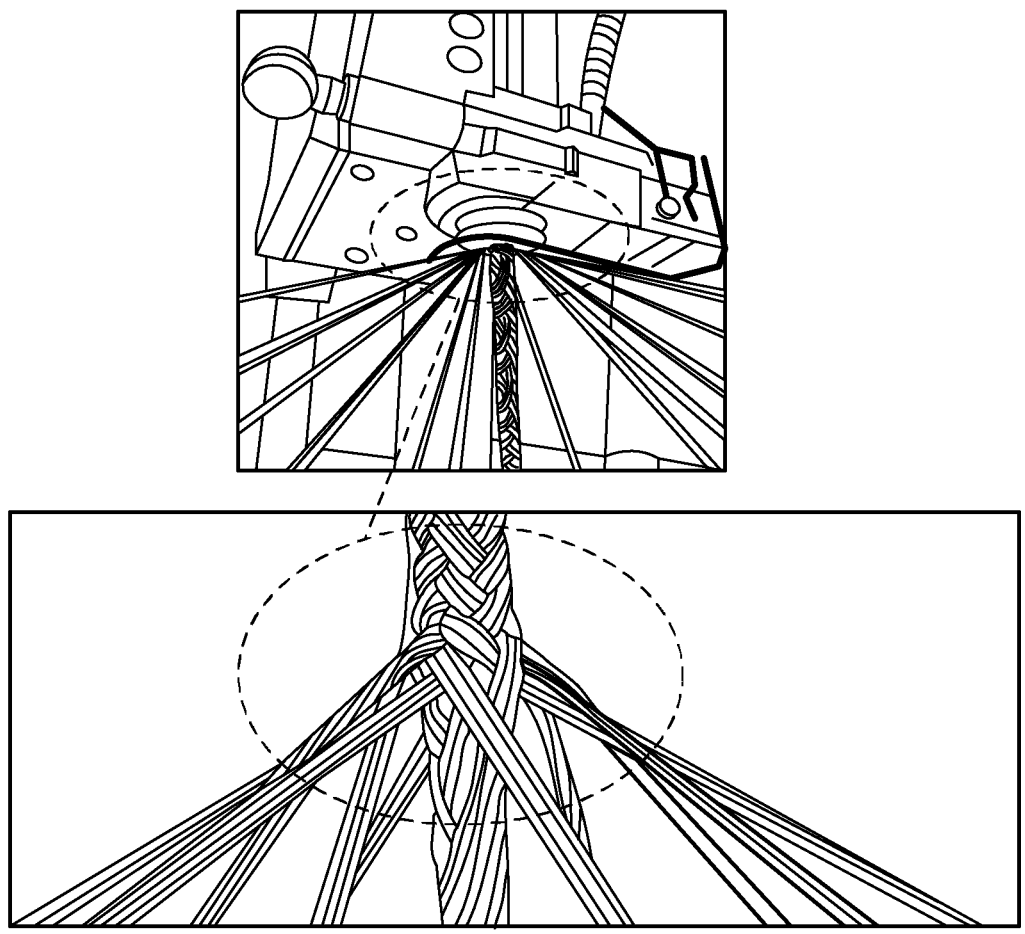
FIG. 10 illustrates exemplary single (discrete) adhesive wound dressing cut from a continuous, hollow, bi-axial braided tube manufacturing method.

Referring to FIG. 10, a single count of an adhesive wound dressing of a specific length may be cut from a continuous hollow bi-axially braided 'tube', in accordance with an embodiment of the present invention. The aforementioned 'tube' may include the first layer, the second layer, and the third layer, in accordance with one embodiment of the present invention.

Figure 14:
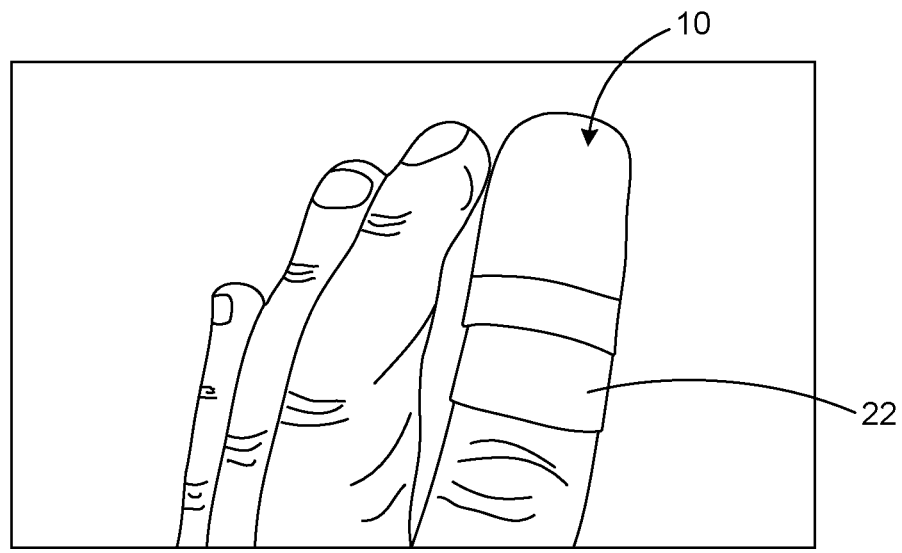
FIGS. 14 and 15 illustrate views of the adhesive wound dressing being deployed on a user's finger.
Figure 15:
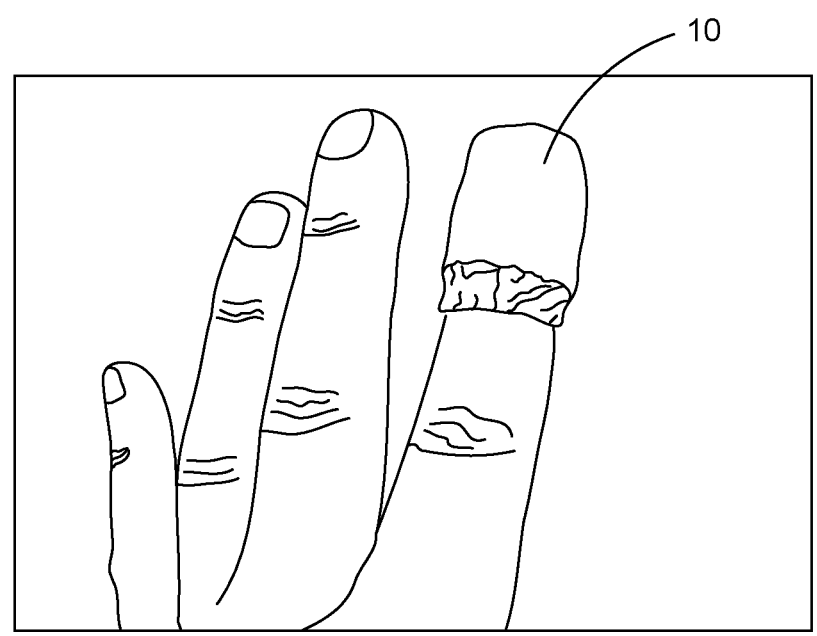

One other alternative method to manufacture the adhesive wound dressing may include the following steps: continuous braiding of the first layer cloth or the outer shell; continuous internal braiding of the second layer; insertion of the gauze inner dressing; splicing of sub-rolls in to master rolls; continuous coating application of the adhesive layer; circumferential application of the removable paper backing; and the control of the speed and tension of the braiding operation to provide one of the 'waisted', 'pinched', 'domed' or closed end; and the cutting individual pieces of the adhesive wound dressing of pre-determined length to define the open end. FIGS. 14 and 15 illustrate views of the adhesive wound dressing manufactured using the aforementioned method steps. In an alternative embodiment, a weaker and color differentiated 'joining lace 28' may be woven in to the adhesive wound dressing during manufacture. The joining lace may be used to release the adhesive wound dressing without resorting to cutting instruments after use.

Figure 11:
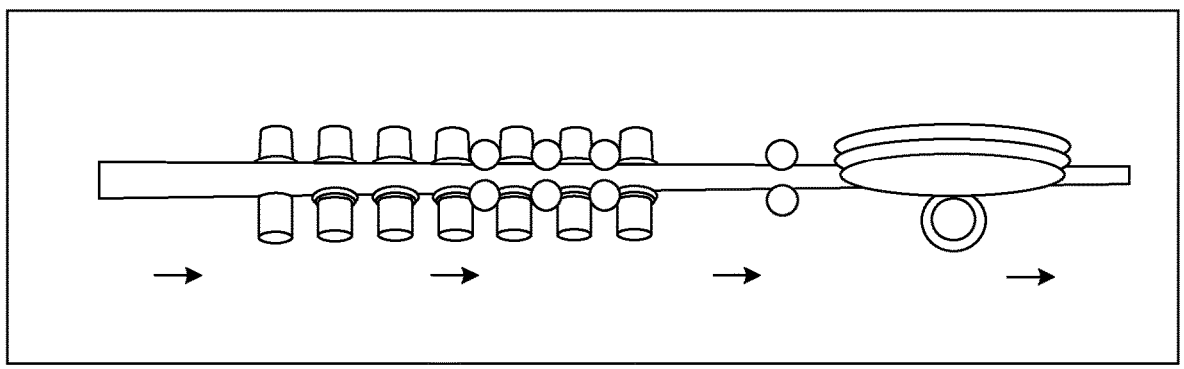
FIG. 11 illustrates alternative, exemplary single (discrete) adhesive wound dressing from a continuous, flat, woven web manufacturing method.

Referring to FIG. 11, another alternative method of manufacturing single discrete pieces of the adhesive wound dressing includes stamping from a continuous flat web including the first layer, the second layer, and the third layer, in which the pre-spaced internal cotton gauze or the third layer may be positioned at regular intervals or in a spaced apart manner. In an embodiment, the edges of the flat web may be progressively curled inwards to form a continuous tube.

Figure 12:
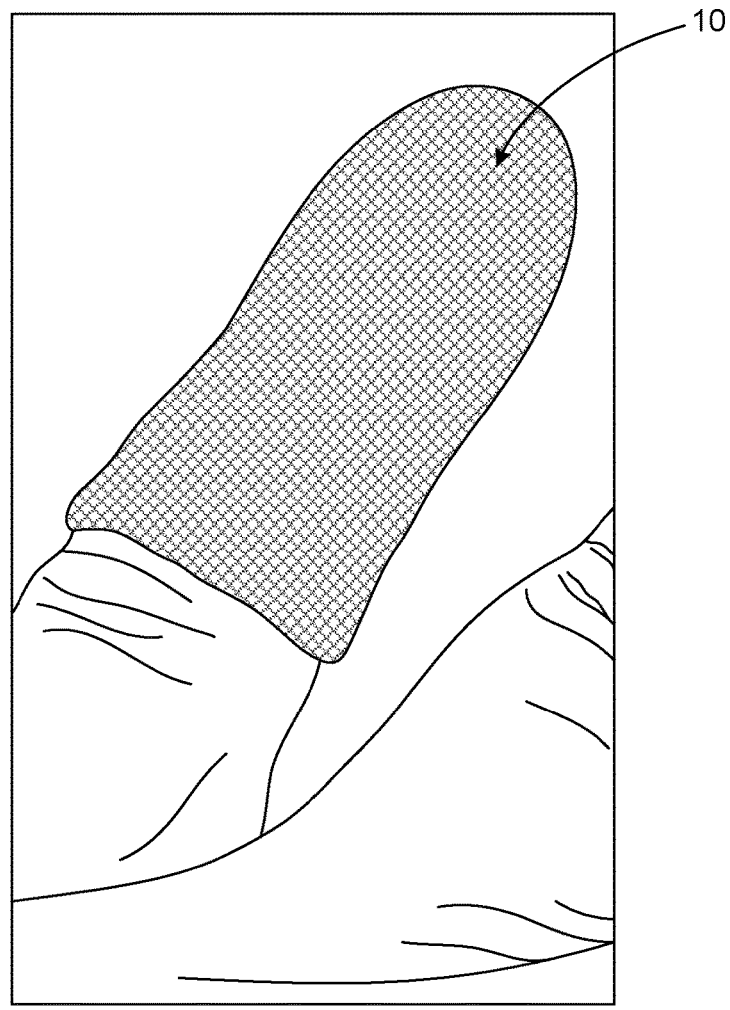
FIG. 12 illustrates alternative exemplary adhesive wound dressing, manufactured using a knitting technique.

Referring to FIG. 12, another alternative method of manufacturing single discrete, adhesive wound dressings includes a knitting or weaving technique. More specifically, the adhesive wound dressing may be manufactured in a similar way as glove fingers are manufactured. Discrete pieces of the adhesive wound dressing may be manufactured from a single shell. In one embodiment, the shell may be designed to absorb the wound fluids and tissue. In an embodiment, the adhesive wound dressing so manufactured may be coated or dipped externally with a hypo-allergenic, non-latex, stretch waterproof coating.

Figure 13:
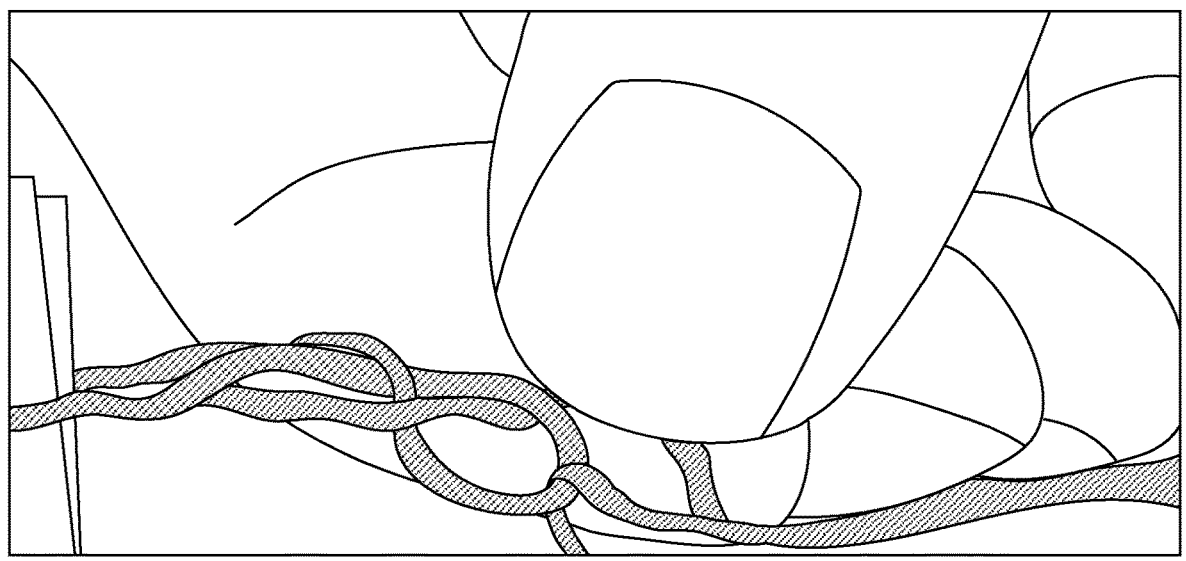
FIG. 13 illustrates a joining lace used in the adhesive wound dressing, in accordance with an embodiment of the present invention.

Referring to FIG. 13, an adhesive wound dressing manufactured via the stamping operation performed on a flat web, which has been progressively funneled in to a tubular shape may be joined by a single weaker woven thread or joining lace 28. The joining lace may be typically color differentiated from the other threads appearing on the adhesive wound dressing. The joining lace may be used to remove the adhesive wound dressing after use without the need to use a separate cutting device such as a pair of scissors.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

It is noted that according to USA law 35 USC § 112 (1), all claims must be supported by sufficient disclosure in the present patent specification, and any material known to those skilled in the art need not be explicitly disclosed. However, 35 USC § 112 (6) requires that structures corresponding to functional limitations interpreted under 35 USC § 112 (6) must be explicitly disclosed in the patent specification. Moreover, the USPTO's Examination policy of initially treating and searching prior art under the broadest interpretation of a "mean for" or "steps for" claim limitation implies that the broadest initial search on 35 USC § 112(6) (post AIA 112(f)) functional limitation would have to be conducted to support a legally valid Examination on that USPTO policy for broadest interpretation of "mean for" claims. Accordingly, the USPTO will have discovered a multiplicity of prior art documents including disclosure of specific structures and elements which are suitable to act as corresponding structures to satisfy all functional limitations in the below claims that are interpreted under 35 USC § 112(6) (post AIA 112(f)) when such corresponding structures are not explicitly disclosed in the foregoing patent specification. Therefore, for any invention element(s)/structure(s) corresponding to functional claim limitation(s), in the below claims interpreted under 35 USC § 112(6) (post AIA 112(f)), which is/are not explicitly disclosed in the foregoing patent specification, yet do exist in the patent and/or non-patent documents found during the course of USPTO searching, Applicant(s) incorporate all such functionally corresponding structures and related enabling material herein by reference for the purpose of providing explicit structures that implement the functional means claimed. Applicant(s) request(s) that fact finders during any claims construction proceedings and/or examination of patent allowability properly identify and incorporate only the portions of each of these documents discovered during the broadest interpretation search of 35 USC § 112(6) (post AIA 112(f)) limitation, which exist in at least one of the patent and/or non-patent documents found during the course of normal USPTO searching and or supplied to the USPTO during prosecution. Applicant(s) also incorporate by reference the bibliographic citation information to identify all such documents comprising functionally corresponding structures and related enabling material as listed in any PTO Form-892 or likewise any information disclosure statements (IDS) entered into the present patent application by the USPTO or Applicant(s) or any $3^{rd}$ parties. Applicant(s) also reserve its right to later amend the present application to explicitly include citations to such documents and/or explicitly include the functionally corresponding structures which were incorporate by reference above.

Thus, for any invention element(s)/structure(s) corresponding to functional claim limitation(s), in the below claims, that are interpreted under 35 USC § 112(6) (post AIA 112(f)), which is/are not explicitly disclosed in the foregoing patent specification, Applicant(s) have explicitly prescribed which documents and material to include the otherwise missing disclosure, and have prescribed exactly which portions of such patent and/or non-patent documents should be incorporated by such reference for the purpose of satisfying the disclosure requirements of 35 USC § 112 (6). Applicant(s) note that all the identified documents above which are incorporated by reference to satisfy 35 USC § 112 (6) necessarily have a filing and/or publication date prior to that of the instant application, and thus are valid prior documents to incorporated by reference in the instant application.

Having fully described at least one embodiment of the present invention, other equivalent or alternative methods of implementing adhesive wound dressing according to the present invention will be apparent to those skilled in the art. Various aspects of the invention have been described above by way of illustration, and the specific embodiments disclosed are not intended to limit the invention to the particular forms disclosed. The particular implementation of the adhesive wound dressing may vary depending upon the particular context or application. By way of example, and not limitation, the adhesive wound dressing described in the foregoing were principally directed to adhesive wound dressing for secure application on wounded body parts of compound shapes; however, similar techniques may instead be applied to self—sealing toy balloons, which implementations of the present invention are contemplated as within the scope of the present invention. The invention is thus to cover all modifications, equivalents, and alternatives falling within the spirit and scope of the following claims. It is to be further understood that not all of the disclosed embodiments in the foregoing specification will necessarily satisfy or achieve each of the objects, advantages, or improvements described in the foregoing specification.

Claim elements and steps herein may have been numbered and/or lettered solely as an aid in readability and understanding. Any such numbering and lettering in itself is not intended to and should not be taken to indicate the ordering of elements and/or steps in the claims.

The corresponding structures, materials, acts, and equivalents of all means or step plus function elements in the claims below are intended to include any structure, material, or act for performing the function in combination with other claimed elements as specifically claimed.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The Abstract is provided to comply with 37 C.F.R. Section 1.72(b) requiring an abstract that will allow the reader to ascertain the nature and gist of the technical disclosure. That is, the Abstract is provided merely to introduce certain concepts and not to identify any key or essential features of the claimed subject matter. It is submitted with the understanding that it will not be used to limit or interpret the scope or meaning of the claims.

The following claims are hereby incorporated into the detailed description, with each claim standing on its own as a separate embodiment.

Only those claims which employ the words "means for" or "steps for" are to be interpreted under 35 USC 112, sixth paragraph (pre AIA) or 35 USC 112(f) post-MA. Otherwise, no limitations from the specification are to be read into any claims, unless those limitations are expressly included in the claims.

What is claimed is:

1. An adhesive wound dressing comprising:
a first layer being an outer layer;
a second layer being a resilient layer and affixed to an inner surface of the first layer;
a third layer being an inner gauze dressing and affixed to an inner surface of the second layer, wherein the first layer, the second layer, and the third layer define a tubular configuration having an open end and a closed end; and
an adhesive layer applied adjacent to the open end, the adhesive layer configured to secure the adhesive wound dressing to a wounded body part subsequent to the wounded body part being inserted within the open end, wherein the second layer includes tubular hollow bi-axially braided cloth scrims configured at discrete locations along the length of the adhesive wound dressing, thereby providing resilience and elasticity to the adhesive wound dressing to secure the adhesive wound dressing on the wounded body part of compound shapes.

2. The adhesive wound dressing according to claim 1, wherein a portion adjacent to the open end is folded, and the adhesive layer is applied on the folded portion.

3. The adhesive wound dressing according to claim 1, wherein the adhesive layer is applied on an inner surface of the third layer adjacent to the open end.

4. The adhesive wound dressing according to claim 2, wherein a removable paper backing is applied on the adhesive layer.

5. The adhesive wound dressing according to claim 3, wherein a removable paper backing having at least one holding tab is applied on the adhesive layer.

6. An adhesive wound dressing comprising:
a first layer being an outer layer;
a second layer being a resilient layer and affixed to an inner surface of the first layer;
a third layer being an inner gauze dressing and affixed to an inner surface of the second layer, wherein the first layer, the second layer, and the third layer define a tubular configuration having an open end and a closed end; and
an adhesive layer applied adjacent to the open end, the adhesive layer configured to secure the adhesive wound dressing to a wounded body part subsequent to the wounded body part being inserted within the open end, wherein the second layer is a hollow bi-axially braided cloth scrim comprising interlocking fibers oriented to provide elasticity in at least two directions, said tubular hollow bi-axially braided cloth scrim being laminated to the first layer.

7. The adhesive wound dressing according to claim 6, wherein the two directions in which the elasticity is provided include longitudinal direction and axial direction of the adhesive wound dressing.

8. The adhesive wound dressing according to claim 1, wherein the first layer comprises a polymeric material.

9. The adhesive wound dressing according to claim 1, wherein the adhesive layer comprises a pressure-sensitive adhesive.

10. An adhesive wound dressing having a tubular configuration, the adhesive wound dressing configured to be applied on wounded body parts of compound shapes, the adhesive wound dressing comprising:
a first layer being an outer layer, the first layer being made of a polymeric material;
a second layer being a resilient layer and affixed to an inner surface of the first layer;
a third layer being an inner gauze dressing and affixed to an inner surface of the second layer, wherein the first layer, the second layer, and the third layer define the tubular configuration having an open end and a closed end; and
an adhesive layer applied adjacent to the open end, the adhesive layer configured to secure the adhesive wound dressing to a wounded body part subsequent to the wounded body part being inserted within the open end, wherein the adhesive layer comprises a pressure-sensitive adhesive,
wherein the second layer includes tubular hollow bi-axially braided cloth scrims configured at discrete locations along the length of the adhesive wound dressing, thereby providing resilience and elasticity to the adhesive wound dressing to secure the adhesive wound dressing on the wounded body.

11. An adhesive wound dressing having a tubular configuration, the adhesive wound dressing configured to be applied on wounded body parts of compound shapes, the adhesive wound dressing comprising:
  a first layer being an outer layer, the first layer being made of a polymeric material;
  a second layer being a resilient layer and affixed to an inner surface of the first layer;
  a third layer being an inner gauze dressing and affixed to an inner surface of the second layer, wherein the first layer, the second layer, and the third layer define the tubular configuration having an open end and a closed end; and
  an adhesive layer applied adjacent to the open end, the adhesive layer configured to secure the adhesive wound dressing to a wounded body part subsequent to the wounded body part being inserted within the open end, wherein the adhesive layer comprises a pressure-sensitive adhesive,
  wherein the second layer is a hollow bi-axially braided cloth scrim comprising interlocking fibers oriented to provide elasticity along a longitudinal direction and an axial direction of the adhesive wound dressing, said tubular hollow bi-axially braided cloth scrim being laminated to the first layer.

12. The adhesive wound dressing according to claim 10, wherein the first layer includes a hypo-allergenic, non-latex, stretch waterproof coating, and at least one gripping portion.

13. An adhesive wound dressing having a tubular configuration, the adhesive wound dressing configured to be applied on wounded body parts of compound shapes, the adhesive wound dressing comprising:
  a first layer being an outer layer, the first layer being made of a polymeric material, and wherein the first layer includes a hypo-allergenic, non-latex, stretch water proof coating and at least one gripping portion;
  a second layer being a resilient layer and affixed to an inner surface of the first layer: wherein the second layer includes tubular hollow bi axially braided cloth scrims configured at discrete locations along the length of the adhesive wound dressing, thereby providing resilience and elasticity to the adhesive wound dressing to secure the adhesive wound dressing on the wounded body part of compound shapes, or wherein the second layer is a hollow bi-axially braided cloth scrim comprising interlocking fibers oriented to provide elasticity along a longitudinal direction and an axial direction of the adhesive wound dressing, said tubular hollow bi-axially braided cloth scrim being laminated to the first layer;
  a third layer being an inner gauze dressing and affixed to an inner surface of the second layer; wherein the first layer, the second layer, and the third layer define the tubular configuration having an open end and a closed end; and
  an adhesive layer applied adjacent to the open end, the adhesive layer configured to secure the adhesive wound dressing to a wounded body part subsequent to the wounded body part being inserted within the open end, wherein the adhesive layer comprises a pressure-sensitive adhesive.

14. The adhesive wound dressing according to claim 6, wherein the first layer comprises a polymeric material.

15. The adhesive wound dressing according to claim 6, wherein the adhesive layer comprises a pressure-sensitive adhesive.

16. The adhesive wound dressing according to claim 6, wherein a portion adjacent to the open end is folded, and the adhesive layer is applied on the folded portion.

17. The adhesive wound dressing according to claim 16, wherein a removable paper backing is applied on the adhesive layer.

18. The adhesive wound dressing according to claim 6, wherein the adhesive layer is applied on an inner surface of the third layer adjacent to the open end.

19. The adhesive wound dressing according to claim 18, wherein a removable paper backing having at least one holding tab is applied on the adhesive layer.

20. The adhesive wound dressing according to claim 11, wherein a removable paper backing is applied on the adhesive layer.

* * * * *